United States Patent [19]

Nienhaus et al.

[11] Patent Number: 4,664,755
[45] Date of Patent: May 12, 1987

[54] PROCESS FOR THE PURIFICATION OF CRUDE β-PHENYLETHYL ALCOHOL

[75] Inventors: Jürgen Nienhaus; Rudolf Hopp, both of Holzminden, Fed. Rep. of Germany

[73] Assignee: Haarman & Reimer GmbH, Holzminden, Fed. Rep. of Germany

[21] Appl. No.: 802,653

[22] Filed: Nov. 27, 1985

[30] Foreign Application Priority Data

Dec. 19, 1984 [DE] Fed. Rep. of Germany ....... 3446265

[51] Int. Cl.$^4$ .............................................. B01D 3/36
[52] U.S. Cl. ...................................... 203/59; 203/63; 203/DIG. 11; 568/810
[58] Field of Search ................. 203/59, 57, 91, 50–52, 203/60, 63, DIG. 11; 568/810, 715, 814

[56] References Cited

U.S. PATENT DOCUMENTS

| | | | |
|---|---|---|---|
| 2,587,753 | 3/1952 | O'Connor et al. | 568/810 |
| 3,893,895 | 7/1975 | Dehnert et al. | 203/59 |
| 4,359,365 | 11/1982 | Deguchi et al. | 203/84 |
| 4,400,558 | 8/1983 | Nemet-Mavrodin et al. | 568/810 |

FOREIGN PATENT DOCUMENTS

| | | | |
|---|---|---|---|
| 1301176 | 9/1961 | France | 203/59 |
| 0136346 | 3/1963 | U.S.S.R. | 568/810 |
| 0652169 | 3/1979 | U.S.S.R. | 203/96 |

OTHER PUBLICATIONS

Chemical Abstracts, vol 93, 1980, p. 464, 93:246446k, Vinnik et al "Study of Azeotropy in Binary Systems Formed by Monoethanolamine and Paraffin Hydrocarbons".
Chemical Abstracts, vol. 77, 1982, p. 405, 139586d, Tatsumi, Japan, Kokai, 62 16,426 "Separatory Purification of Styrene".
Derwent Reports—Abstract 59181T "Separation and Purification of Styrene".
Chemical Abstracts, vol. 69, 1968, p. 6591, 70459e, Efimenko et al "Purificaton of B–Brazan (Benzo[b]Naphtho[2,3–d]–furan) by Azeotropic Rectification".

Primary Examiner—S. Leon Bashore
Assistant Examiner—V. Monoharan
Attorney, Agent, or Firm—Sprung Horn Kramer & Woods

[57] ABSTRACT

Process for the purification of crude β-phenylethyl alcohol by azeotropic distillation in the presence of alkanolamines in which the alkylene chain contains 2 to 4 carbon atoms and is optionally substituted by 1 to 4 $C_1$–$C_3$-alkyl groups.

9 Claims, No Drawings

PROCESS FOR THE PURIFICATION OF CRUDE β-PHENYLETHYL ALCOHOL

The invention relates to a new process for the purification of crude β-phenylethyl alcohol by azeotropic distillation.

Phenylethyl alcohol is a cheap fragrance having a mild odour of roses. Its content in fragrance compositions can be 5 to 20% by weight and sometimes even more than 20% by weight. Because of its mild odour and the relatively high amounts employed, this fragrance has to meet stringent requirements in regard to purity.

Crude β-phenylethyl alcohol is obtained industrially on a fairly large scale as a by-product in the noncatalytic aerial oxidation of ethylbenzene and in the epoxidation of olefinically unsaturated compounds, for example propylene, by means of ethylbenzene hydroperoxide. The crude β-phenylethyl alcohol obtained in this manner cannot be purified by distillation to such an extent that it can be used as a fragrance. In order to obtain a product satisfactory from the point of view of odour, the crude β-phenylethyl alcohol must be subjected to special purification processes. It is suggested in accordance with U.S. Pat. No. 4,400,558 that an insoluble metal halide/β-phenylethyl alcohol adduct, preferably a calcium chloride/phenylethyl alcohol adduct, should be prepared, and this should be separated off and the alcohol liberated from it. Although the purity of the β-phenylethyl alcohol obtained in this manner is entirely satisfactory, the process is very expensive.

The purification of the crude β-phenylethyl alcohol by distillation in the presence of water, glycerol, an alkylene glycol, a polyalkylene glycol, an alkylene glycol monomethyl monoalkyl ether, a polyalkylene glycol monoalkyl ether or a mixture of at least two of these compounds is described in U.S. Pat. No. 4,359,365. If the distillation is carried out in the presence of a solvent having a boiling point higher than that of β-phenylethyl alcohol, an extractive distillation is involved; if the boiling point of the solvent is lower than that of β-phenylethyl alcohol, an azeotropic distillation is involved. Admittedly the process provides β-phenylethyl alcohol of the desired purity, but, since the selectivity of the compounds to be used as an azeotropic or extractive solvent is insufficient, the distillation involves considerable losses of β-phenylethyl alcohol (about 15 to 20% by weight of the β-phenylethyl alcohol present in the crude product is lost).

It has now been found, surprisingly, that, if certain alkanolamines are used as the azeotropic solvent for the distillation of crude β-phenylethyl alcohol, not only is β-phenylethyl alcohol of the desired purity obtained, but, at the same time, these alkanolamines have a substantially higher selectivity than the compounds recommended in U.S. Pat. No. 4,359,365 as auxiliary solvents for the distillation, and it is therefore possible to reduce the distillation losses of β-phenylethyl alcohol to less than 5% by weight.

The invention therefore relates to a process for the purification of crude β-phenylethyl alcohol by azeotropic distillation, which is characterised in that the crude β-phenylethyl alcohol is distilled in the presence of alkanolamines in which the alkylene chain has 2 to 4 carbon atoms and is optionally substituted by 1 to 4 $C_1$-$C_3$-alkyl groups.

Ethanolamine has already been suggested as an auxiliary for the azeotropic distillation of hydrocarbons (see Zh. Prikl. Khim. (Leningrad) 1980, 53 (10), 2388; CA 93, (1980) 246446 k; and Japan. Kokai 72/16,246; CA 77, (1972) 139586 d) and for the purification of B-brazan (benzo[b]naphtho[2,3-d]furan) (see Koks. Khim. 1968 (1) 41–43; and CA 69, (1968) 70459 e). However, since ethanolamine is mentioned in these publications as of equal value with ethylene glycols, polyethylene glycols, alkylamines and alkylenediamines, and since these auxiliary solvents are unsuitable for the azeotropic distillation of β-phenylethyl alcohol because of their inadequate selectivity, the special suitability for the azeotropic distillation of β-phenylethyl alcohol of the aminoalcohols to be used in accordance with the invention, particularly 2-aminoethanol, could not in any way have been foreseen from these publications.

The alkanolamines to be employed in accordance with the invention as auxiliary solvents in the azeotropic distillation of β-phenylethyl alcohol have a boiling point below that of β-phenylethyl alcohol (219.8° C.). The following are examples of alkanolamines of this type: 2-aminoethanol, 1-aminopropan-2-ol, 2-aminopropan-1-ol, 2-aminobutan-1-ol, 1-aminobutan-2-ol, 2-aminopentan-1-ol, 3-aminopentan-2-ol, 1-amino-3-methylbutan-2-ol, 2-amino-2-methylpropan-1-ol, 3-aminopropan-1-ol, 2-aminobutan-3-ol, 3-aminobutan-1-ol, 1-amino-3-methylbutan-3-ol, 1-amino-2,2-dimethylpropan-3-ol, 2-amino-3-methylhexan-4-ol, 2-amino-2,4-dimethylpentan-4-ol and 4-aminobutan-1-ol. Alkanolamines which are used preferentially are 2-aminoethanol, 1-aminopropan-2-ol and 3-aminopropan-1-ol.

The amount of alkanolamine can be varied within a wide range; it has proved suitable to employ the alkanolamines in an amount of 0.1 to 10 parts by weight, preferably 0.1 to 1 part by weight, per part by weight of crude β-phenylethyl alcohol.

The process according to the invention can be carried out continuously or discontinuously. In the latter case, crude β-phenylethyl alcohol and the alkanolamine are initially taken and are subjected to fractional distillation in a multi-plate column. The impurities, together with the alkanolamine, are taken off at the top of the column as the first fraction. This is followed by a small intermediate fraction which, in addition to the alkanolamine, already contains a little β-phenylethyl alcohol and can be re-employed in the next distillation; finally, β-phenylethyl alcohol of satisfactory quality for perfumes is taken off. The distillation is carried out under the conditions customary for the distillation of β-phenylethyl alcohol, that is to say either under normal pressure or a reduced pressure of 1 to 1000 mbar and at a temperature of 50° to 220° C. It is preferable to maintain a reflux ratio of 0.1:1 to 50:1, preferably 1:1 to 10:1.

In the continuous distillation, the crude β-phenylethyl alcohol and the alkanolamine are fed into the middle of an azeotropic distillation column. The azeotrope consisting of alkanolamine and impurities is taken off at the top of the column and the purified β-phenylethyl alcohol is taken off at the bottom of the column. The β-phenylethyl alcohol thus purified is then subjected to a second fractional distillation. The distillation conditions (pressure, temperature and reflux ratio) are similar to the conditions indicated above for the discontinuous distillation.

EXAMPLE 1

600 g of crude β-phenylethyl alcohol containing about 8 to 10% by weight of impurities, and 200 g of 2-aminoethanol are mixed and are distilled through a 1 m packed column at a pressure of 100 mbar, a 10:1 reflux ratio being maintained.

The first runnings amount to 194 g; they pass over at a bottom temperature of 129° to 150° C. and a head temperature of 110° C. According to analysis by gas chromatography, this product consists of 89% by weight of 2-aminoethanol and 11% by weight of impurities. It contains no β-phenylethyl alcohol.

80 g of an intermediate fraction then pass over at a bottom temperature of 151° C. and a head temperature of 110° to 145° C. According to analysis by gas chromatography, this intermediate fraction consists of 33% by weight of 2-aminoethanol, 62% by weight of β-phenylethyl alcohol and 5% by weight of impurities.

The main fraction (482 g) passes over after this intermediate fraction. In the course of this, the bottom temperature rises to 180° C.; the head temperature is 145° C. According to analysis by gas chromatography, the main fraction consists of 99.9% by weight of β-phenylethyl alcohol. This β-phenylethyl alcohol is satisfactory from the point of view of odour and can be used as a fragrance.

41 g of distillation residue remain in the sump.

EXAMPLE 2

Distillation is carried out as described in Example 1, only using an equal amount of 3-aminopropan-1-ol instead of the 200 g of 2-aminoethanol. 185 g of first running are obtained; they pass over at a bottom temperature of 125° to 150° C. and a head temperature of 120° C. According to analysis by gas chromatography, this product consists of 89% by weight of 3-aminopropanol and 11% by weight of impurities. The amount of the intermediate fraction is 85 g; it passes over at a bottom temperature of 150° C. and a head temperature of 120° to 145°. According to analysis by gas chromatography, it consists of 36% by weight of 3-aminopropanol, 60% by weight of β-phenylethyl alcohol and 4% by weight of impurities. The main fraction amounts to 475 g; it passes over at a bottom temperature of 145° to 180° C. and a head temperature of 150° C. According to analysis by gas chromatography, the main fraction consists of 99.9% by weight of β-phenylethyl alcohol; the β-phenylethyl alcohol is satisfactory from the point of view of odour and can be used as a fragrance. The distillation residue is 49 g.

EXAMPLE 3

The distillation is carried out as described in Example 1, only using an equal amount of 1-aminopropan-2-ol instead of the 200 g of 2-aminoethanol.

190 g of first runnings are obtained; these pass over at a bottom temperature of 130° to 150° C. and a head temperature of 96° to 100° C. According to analysis by gas chromatography, this product consists of 90% by weight of 1-aminopropan-2-ol and 10% by weight of impurities.

The amount of intermediate fraction is 90 g; it passes over at a bottom temperature of 150° C. and a head temperature of 100° to 145° C. According to analysis by gas chromatography, it consists of 32% by weight of 1-aminopropan-2-ol, 59% by weight of β-phenylethyl alcohol and 9% by weight of impurities. The main fraction amounts to 470 g; it passes over at a bottom temperature of 150° to 180° C. and a head temperature of 145° C. According to analysis by gas chromatography, it consists of 99.9% by weight of β-phenylethyl alcohol. The β-phenylethyl alcohol is satisfactory from the point of view of odour and can be used without further purification as a fragrance.

The distillation residue is 43 g.

What is claimed is:

1. In a process for the purification of crude β-phenyethyl alcohol containing impurities by azeotropic distillation in a column in the presence of a solvent, the improvement which comprises using as the solvent an alkanolamine in which the alkylene chain has 2 to 4 carbon atoms and is unsubstituted or substituted by 1 to 4 $C_1$-$C_3$-alkyl groups, said alkanolamine forming an azeotrope with the impurities, taking off said azeotrope at the top of the column and taking off the purified β-phenylethyl alcohol at the bottom of the column for distillation that is carried out continuously, and taking off at the top of the column first said azeotrope and subsequently the purified β-phenylethyl alcohol for distillation that is carried out discontinuously.

2. The process of claim 1, wherein the alkanolamine is employed in an amount of 0.1 to 10 parts by weight per part by weight of crude β-phenylethyl alcohol.

3. A process according to claim 1, wherein the alkanolamine is employed in an amount of 0.1 to 1 part by weight per part by weight of crude β-phenylethyl alcohol.

4. A process according to claim 1, wherein the process is conducted at a temperature of 50° to 220° C.

5. A process according to claim 1, wherein a reflux ratio of 0.1:1 to 50:1 is maintained.

6. A process according to claim 1, wherein a reflux ratio of 1:1 to 10:1 is maintained.

7. A process according to claim 1, wherein the alkanolamine is selected from the group consisting of 2-aminoethanol, 1-aminopropan-2-ol, 2-aminopropan-1-ol, 2-aminobutan-1-ol, 1-aminobutan-2-ol, 2-aminopentan-1-ol, 3-aminopentan-2-ol, 1-amino-3-methylbutan-2-ol, 2-amino-2-methylpropan-1-ol, 3-aminopropan-1-ol, 2-aminobutan-3-ol, 3-aminobutan-1-ol, 1-amino-3-methylbutan-3-ol, 1-amino-2,2-dimethylpropan-3-ol, 2-amino-3-methylhexan-4-ol, 2-amino-2,4-dimethylpentan-4-ol and 4-aminobutan-1-ol.

8. The process of claim 7, wherein the alkanolamine is selected from the group consisting of 2-aminoethanol, 1-aminopropan-2-ol or 3-aminopropan-1-ol.

9. The process of claim 7, wherein the alkanolamine is 2-aminoethanol.

* * * * *